(12) United States Patent
Erkens et al.

(10) Patent No.: US 10,098,819 B2
(45) Date of Patent: Oct. 16, 2018

(54) COMPOSITIONS AND METHODS FOR LIGHTENING THE COLOR OF KERATINIC FIBERS

(71) Applicant: Henkel AG & Co. KGaA, Duesseldorf (DE)

(72) Inventors: Udo Erkens, Willich (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/526,585

(22) PCT Filed: Oct. 2, 2015

(86) PCT No.: PCT/EP2015/072831
§ 371 (c)(1),
(2) Date: May 12, 2017

(87) PCT Pub. No.: WO2016/074854
PCT Pub. Date: May 19, 2016

(65) Prior Publication Data
US 2017/0333303 A1 Nov. 23, 2017

(30) Foreign Application Priority Data
Nov. 12, 2014 (DE) .................. 10 2014 223 092

(51) Int. Cl.
| | | |
|---|---|---|
| *A61K 8/11* | (2006.01) |
| *A61K 8/73* | (2006.01) |
| *A61K 8/81* | (2006.01) |
| *A61K 8/23* | (2006.01) |
| *A61Q 5/08* | (2006.01) |

(52) U.S. Cl.
CPC .................. *A61K 8/11* (2013.01); *A61K 8/23* (2013.01); *A61K 8/73* (2013.01); *A61K 8/8135* (2013.01); *A61Q 5/08* (2013.01); *A61K 2800/882* (2013.01)

(58) Field of Classification Search
None
See application file for complete search history.

(56) References Cited

FOREIGN PATENT DOCUMENTS

| DE | 196 13 941 A1 * | 10/1997 | ............... A61K 8/22 |
|---|---|---|---|
| DE | 19613941 A1 | 10/1997 | |
| EP | 0493392 B1 | 3/1996 | |
| EP | 1510529 A1 | 3/2005 | |
| WO | 2005084618 A1 | 9/2005 | |
| WO | WO 2005/084618 A1 * | 9/2005 | ............... A61K 8/11 |

OTHER PUBLICATIONS

EPO, International Search Report and Written Opinion issued in International Application No. PCT/EP2015/072831, dated Dec. 2, 2015.

* cited by examiner

*Primary Examiner* — Aradhana Sasan
(74) *Attorney, Agent, or Firm* — Lorenz & Kopf, LLP

(57) ABSTRACT

Cosmetic composition for lightening the color of keratinic fibers, including at least two separately packaged formulations (A) and (B) which are mixed immediately prior to application to give an application mixture, wherein the formulation (A), based on its total weight, contains from about 10% to about 99% by weight of peroxodisulfate(s), and the formulation (B) is a free-flowing composition comprising water and at least one oxidizing agent, characterized in that the formulation (A) has been packaged in a water-soluble film including, based on its total weight, at least about 60% by weight of a polymer mixture having a multimodal molecular weight distribution, feature above-average application properties.

13 Claims, No Drawings

COMPOSITIONS AND METHODS FOR LIGHTENING THE COLOR OF KERATINIC FIBERS

CROSS-REFERENCE TO RELATED APPLICATION

This application is a U.S. National-Stage entry under 35 U.S.C. § 371 based on International Application No. PCT/EP2015/072831, filed Oct. 2, 2015, which was published under PCT Article 21(2) and which claims priority to German Application No. 10 2014 223 092.6, filed Nov. 12, 2014, which are all hereby incorporated in their entirety by reference.

TECHNICAL FIELD

The present disclosure relates to a cosmetic composition comprising a cosmetic formulation packaged in a water-soluble and/or water-dispersible casing and a method for the blonding of keratinic fibers.

BACKGROUND

In the field of decorative cosmetics, in particular cosmetics for the bleaching or the coloring of hair, there is a great demand for effective products that are both easy to handle and safe. Provided to the consumer by the field of hair cosmetics in particular are systems quite effective for hair lightening and coloring, but the improper use of them, for instance contact with areas of skin or the eyes, can lead to irritation and in extreme cases even to the triggering of allergies. There exists, therefore, a great demand for ensuring the safe handling of such cosmetic formulations in addition to putting an easily dispensed packaging system in the hands of the consumer, which also allows the necessary components to be mixed together or combined at the place of use. In this context, the avoidance of product dust is an important point, particularly in regard to bleaching or lightening hair cosmetics.

The literature contains initial attempts at solving the previously described technical problems. Thus, German Patent Application DE 196 13 941 A1 describes a method for the preparation of nondusting pulverulent compositions for hair blonding. The blonding compositions have at least one peroxide compound, which is admixed with suitable thickeners and then packaged in portions in water-soluble sachets for transportation and further processing.

European Patent EP 493 392 B1 discloses means for hair bleaching and dyeing that are incorporated into polyvinyl alcohol packaging in order to reduce the irritation caused by powder dust.

European Patent Application EP 1 510 529 A1 describes the preparation of multimodal dispersions of vinyl alcohol/vinyl acetate copolymers.

Portion-sized cosmetic formulations disclosed in the prior art indeed offer improved handling and a reduction in the dust contamination coming from packaged cosmetic formulations, but the product portions packaged in water-soluble film systems pose the disadvantage of only slowly dissolving in water.

BRIEF SUMMARY

Cosmetic compositions and methods for changing the color of keratinic fibers are provided herein. In an embodiment, a cosmetic composition for lightening the color of keratinic fibers includes at least two separately packaged formulations (A) and (B), which are mixed immediately prior to application to give an application mixture. The formulation (A), based on its total weight, includes from about 10 to about 99% by weight peroxydisulfate(s). The composition (B) is a flowable composition including water and at least one oxidizing agent. Formulation (A) has been packaged in a water-soluble film including, based on its total weight, at least about 60% by weight of a polymer mixture having a multimodal molecular weight distribution.

In another embodiment, a method for changing the color of keratinic fibers includes mixing at least two separately packaged formulations (A) and (B) immediately prior to application to give an application mixture. The formulation (A), packaged in a water-soluble film, is dissolved and incorporated into the formulation (B). The formulation (A), based on its total weight, includes from about 10 to about 99% by weight peroxydisulfate(s). The formulation (B) is a flowable composition including water and at least one oxidizing agent. Formulation (A) has been packaged in a water-soluble film including, based on its total weight, at least about 60% by weight of a polymer mixture having a multimodal molecular weight distribution.

In another embodiment, a cosmetic composition for lightening the color of keratinic fibers includes at least two separately packaged formulations (A) and (B), which are mixed immediately prior to application to give an application mixture. The formulation (A), based on its total weight, includes from about 15 to about 99% by weight peroxydisulfate(s). The composition (B) is a flowable composition that includes water and at least one oxidizing agent. Formulation (B) includes, based on its weight, less than about 20% by weight fatty substances. The weight ratio of formulation (A) to formulation (B) is about 2:1 to about 1:100. Formulation (A) has been packaged in a water-soluble film including, based on its total weight, at least about 60% by weight of a polymer mixture having a multimodal molecular weight distribution. The polymer mixture has a polydispersity index of greater than about 2.2. The water-soluble film has a thickness from about 0.01 to about 0.1 mm.

DETAILED DESCRIPTION

The following detailed description is merely exemplary in nature and is not intended to limit the hair treatment agents and methods for treating hair. Furthermore, there is no intention to be bound by any theory presented in the preceding background or the following detailed description.

An object of the present disclosure is to provide portion-sized cosmetic formulations for bleaching keratinic fibers that are simple, safe and easy to handle, and the handling of which can take place, for example, without dust being generated while supplying the consumer an application mixture ready for use within a short period of time.

It has been found that the aforementioned problems can be solved by using special packaging. Said packaging not only avoids the generation of dust, but additionally enables the surprisingly quick and residue-free production of the cosmetic hair application mixture.

A first object of the present disclosure is a cosmetic composition for lightening the color of keratinic fibers containing at least two separately packaged formulations (A) and (B), which are mixed immediately prior to application to give an application mixture, whereby the formulation (A), based on its total weight, contains about 10 to about 99% by weight peroxydisulfate(s)

the formulation (B) is a flowable composition comprising water and at least one oxidizing agent, wherein formulation (A) has been packaged in a water-soluble film including, based on its total weight, to an extent of at least about 60% by weight of a polymer mixture having a multimodal molecular weight distribution.

The molecular weight distribution of the polymer mixture contained in the water-soluble film is multimodal. In other words, the density of the molecular weight frequency distribution shows at least two modes (maxima), for example two, three, four, five or more modes. Particularly preferable is a bimodal molecular weight distribution because, as described above, on the one hand it has a beneficial effect on the product properties of the cosmetic composition as contemplated herein, and, on the other hand, it is easier to implement than a tri- or multi-modal frequency distribution.

The preferred bimodal molecular weight distribution can be symmetric or asymmetric.

In a preferred multimodal, preferably bimodal molecular weight distribution, the molecular weights of at least two of the maxima differ by from about 5% to about 120%, preferentially by from about 10% to about 90% and in particular from about 20% to about 60% based on the smallest identifiable modal molecular weight.

In a further preferred multimodal, preferably bimodal molecular weight distribution, the frequency of the minimum found between two maxima differs from the frequency of the smaller of these two maxima (the maximum with the lower frequency) by from about 5% to about 80%, preferably from about 10% to about 60% and in particular from about 20% to about 40%, each based on the frequency of the smaller of the two maxima.

In regard to the application properties of the composition as contemplated herein, in particular the quick and residue-free production of the cosmetic hair application mixture, it has been shown to be advantageous for the water-soluble film to include at least about 70% by weight, preferably of at least about 80% by weight, more preferably of at least about 90% by weight, and in particular of at least about 95% by weight of a polymer mixture having a multimodal molecular weight distribution. A bimodal molecular weight distribution is in turn preferential.

Advantageous in regard to product properties are polymer mixtures having a polydispersity index of greater than about 2.2, preferably greater than about 3.0, and in particular greater than about 4.6. In this context, polydispersity refers to the relationship between the weight average molecular weight and the number average molecular weight.

The weight average molecular weight (Mmit) is defined as Mmit=$\Sigma$ni Mi2/$\Sigma$ni Mi where Mmit=weight average molar mass, Ni=the number of macromolecules in the sample having exactly i repeating units and Mi=molecular weight i.

The weight average is obtained by methods taking into account the size and shape of a molecule in solution, for example static light scattering, small angle x-ray scattering, and sedimentation equilibrium measurements.

The number average molecular weight (Mn) is defined as Mn=$\Sigma$ni Mi2/$\Sigma$ni Mi where Mn=number average molar mass, ni=the number of macromolecules in the sample having exactly i repeating units and Mi=molecular weight i.

The number average can be determined using colligative methods such as cryoscopy and membrane or vapor pressure osmometry, and—as long as the number of end groups per molecule is known—by end-group analysis.

Water-soluble films not composed entirely of the polymer mixture with the multimodal molecular weight distribution may contain additional active ingredients or fillers as well as solvents, in particular water, as additional ingredients.

Thus, included among the group of additional ingredients are, for example, components having a hair cosmetic effect as well as materials which protect the ingredients of preparation (A) enclosed in within the film material against decomposition or deactivation due to light irradiation. Antioxidants, UV absorbers and fluorescent dyes have proven to be particularly suitable in this regard.

Based on its total weight, the water-soluble film preferably has a water content of about 3.0 to about 12% by weight, more preferably from about 4.0 to about 10% by weight.

The thickness of the water-soluble film used for packaging preparation (A) preferably measures about 0.01 to about 0.1 mm, more preferably from about 0.01 to about 0.08 mm, and in particular from about 0.02 to about 0.06 mm.

The water-soluble film within which preparation (A) is packed may comprise one or more structurally varying water-soluble polymers. Particularly suitable as water-soluble polymer(s) are polymers chosen from the group of (optionally acetalyzed) polyvinyl alcohols (PVAL), polyvinylpyrrolidone, polyethylene oxide, gelatin and cellulose.

In a first preferential embodiment, the polymer mixture with the multimodal and preferably bimodal molecular weight distribution comprises to two vinyl acetate/vinyl alcohol copolymers. Therefore, the preferential cosmetic compositions are characterized by the polymer blend including, based on its total weight, of a mixture comprising at least about 60% by weight, preferably at least about 80% by weight, more preferably at least about 90% by weight, quite preferably at least about 95% by weight a1) water-soluble vinyl alcohol/vinyl acetate copolymer a1) and a2) at least one water-soluble vinyl alcohol/vinyl acetate copolymer a2) different from the water-soluble vinyl alcohol/vinyl acetate copolymer a1).

In the aforementioned preferential embodiment based on two water-soluble vinyl alcohol/vinyl acetate copolymers, the polymer blend preferably has a polydispersity index greater than 2.2, more preferably greater than about 3.0, and in particular greater than about 4.6, whereas the polydispersity index of the vinyl alcohol/vinyl acetate copolymer a1) is preferably between about 1.8 and about 2.3.

Particularly advantageous product properties are to be achieved using vinyl alcohol/vinyl acetate copolymers a1) having a degree of hydrolysis between about 84% and about 90%, preferably between about 85% and about 89%, and in particular between about 86% and about 88%. In other words, the corresponding copolymers a1) exhibit a residual content of acetyl groups of between about 10% and about 16%, preferably of between about 11% and about 15%, and in particular of between about 12% and about 14%.

In addition to the polydispersity index and the degree of hydrolysis, the viscosity of aqueous solutions of the vinyl alcohol/vinyl acetate has also proven to be a distinguishing feature of particularly advantageous copolymers. Therefore, preferred cosmetic compositions are characterized in that the vinyl alcohol/vinyl acetate copolymer a1) has a viscosity (20° C., 4% by weight solution in water, measured using a Brookfield LV Viscosimeter with UL adapter) of between about 12 cP and about 20 cP, preferably of between about 14 cP and about 19 cP, and in particular of between about 16 cP and about 18 cP.

In comparison, the vinyl alcohol/vinyl acetate copolymer a2) (20° C., 4% by weight solution in water, measured using a Brookfield LV Viscosimeter with UL adapter) preferably has a viscosity of between about 20 cP and about 30 cP, preferably of between about 20 cP and about 28 cP, and in particular of between about 20 cP and about 25 cP.

In addition to the previously described combination of two vinyl alcohol/vinyl acetate copolymers, additional preferable polymer combinations exist having properties advantageous with regard to the aforementioned technical functions. In an alternative preferential embodiment of the cosmetic compositions as contemplated herein, the polymer mixture includes, based on its total weight, of a mixture comprising at least about 60% by weight, hence preferably at least about 80% by weight, more preferably at least about 90% by weight, and particularly preferably at least about 95% by weight
- a1) water-soluble vinyl alcohol/vinyl acetate copolymer a1) and
- a2) at least one optionally modified water-soluble polysaccharide, preferably at least one water-soluble polysaccharide chosen from the group of methyl cellulose, carboxymethyl cellulose, ethyl cellulose, hydroxyethyl cellulose, hydroxypropyl cellulose, hydroxypropyl methylcellulose, dextrin, and hydroxypropyl starch, particularly preferably at least one water-soluble polysaccharide from the group of hydroxypropyl starches.

On the other hand, the polydispersity index of the aforementioned polymer mixtures of vinyl alcohol/vinyl acetate copolymers and polysaccharide is preferably greater than about 2.2, more preferably greater than about 3.0, and in particular greater than about 4.6, whereas the polydispersity index of the vinyl alcohol/vinyl acetate copolymer a1) in these mixtures is preferably between about 1.8 and about 2.3.

If the vinyl alcohol/vinyl acetate copolymer a1) is combined with a polysaccharide, then the vinyl alcohol/vinyl acetate copolymer a1) exhibits a degree of hydrolysis between about 84% and about 90%, preferably between about 85% and about 89%, and in particular between about 86% and about 88%. The viscosity of the vinyl alcohol/vinyl acetate copolymer a1) (20° C., 4% by weight solution in water, measured using a Brookfield LV Viscosimeter with UL adapter) is preferably between about 12 cP and about 20 cP, more preferably between about 14 cP and about 19 cP, and in particular between about 16 cP and about 18 cP.

In addition to the water-soluble films described above, the cosmetic compositions as contemplated herein comprise the preparations (A) and (B). In regard to the dissolution behavior and functional behavior of said compositions, it has proven advantageous for the weight ratio of formulation (A) to formulation (B) to be from about 2:1 to about 1:100, preferably from about 2:1 to about 1:10, and in particular from about 2:1 to about 1:3.

The composition (A) contains as a characteristic component from about 10 to about 99% by weight peroxydisulfate(s), whereby the proportion by weight of peroxydisulfate(s) is preferably from about 15 to about 99% by weight, and in particular from about 20 to about 45% by weight.

Peroxydisulfates preferable for use are the alkali metal and ammonium peroxydisulfates, in particular sodium peroxydisulfate, potassium peroxydisulfate, ammonium peroxydisulfate and mixtures thereof. In principle, the weight ratios of the various peroxydisulfates may be freely chosen, but they may also be determined within predefined limits. For example, the quantity of potassium peroxydisulfate used may always be kept higher than the given amount of sodium peroxydisulfate and ammonium peroxydisulfate used. Exemplary of this, an embodiment of the cosmetic composition as contemplated herein will be explicated in which the formulation (A), based on its weight, contains from about 10 to about 80% by weight, preferably from about 25 to about 70% by weight, more preferably from about 40 to about 60% by weight potassium peroxydisulfate, and/or the ratio by weight of the quantity of potassium peroxydisulfate contained in the composition to the total quantity of peroxydisulfates contained in the composition is at least about 0.5, preferably at least about 0.7 and more preferably at least about 0.9.

The formulation (A) preferably exists in solid form, for example in the form of a powder, a granulate or a compressed body, for example in the form of a tablet. Preferential cosmetic formulations (A) exist in powder form.

Prior to being applied to the hair, the formulation (A) is preferably mixed with and dissolved in the aqueous formulation (B). A distinguishing component of the aqueous composition (B) is at least one oxidizer. In a preferred embodiment, the composition (B) is an aqueous solution of hydrogen peroxide. Preferable is a formulation (B), which, based on its weight, contains about 50 to about 98% by weight, preferably about 60 to about 95% by weight, more preferably about 80 to about 95% by weight water, and, calculated as 100% H2O2, contains about 0.5 to about 20% by weight, preferably about 1 to about 15% by weight, and particularly preferably about 2 to about 12% by weight hydrogen peroxide.

As an additional component, the composition (B) preferably contains emulsifiers or surface-active agents.

Preferred as a first group are the anionic surfactants. In terms of the present disclosure, anionic surfactants are all anionic surface-active substances suitable for use on the human body. Such substances are characterized by a water-solubilizing anionic group such as, for example, a carboxylate, sulfate, sulfonate or phosphate group and a lipophilic alkyl group comprising around 8 to 30 carbon atoms. In addition, glycol or polyglycol ether groups and ester, ether and amide groups as well as hydroxyl groups may also be present in the molecule. Examples of such anionic surfactants, each in the form of the sodium, potassium and ammonium salts as well as the mono-, di- and trialkanolammonium salts comprising 2 to 4 carbon atoms in the alkanol group, are linear and branched fatty acids comprising 8 to 30 carbon atoms (soaps); ether carboxylic acids, in particular of the formula $RO(CH_2CH_2O)_xCH_2COOH$, in which R is a linear alkyl group comprising 8 to 30 carbon atoms and x=0 or from 1 to 16; acyl sarcosides; acyl taurides; acyl isethionates; sulfosuccinic acid mono- and dialkylesters as well as sulfosuccinic acid monoalkyl polyoxyethyl esters; linear alkane sulfonates; linear α-olefin sulfonates; sulfonates of unsaturated fatty acids; α-sulfofatty acid methyl esters of fatty acids; alkyl sulfates and alkyl ether sulfates, in particular of the formula $RO(CH_2CH_2O)_xSO_3H$, in which R stands for a linear alkyl group comprising 8 to 30 carbon atoms and x stands for 0 or a number from 1 to 12; mixtures of surface-active hydroxysulfonates; sulfated hydroxyalkyl polyethylene- and/or hydroxyalkylene propylene glycol ethers; esters of tartaric acid and citric acid with alcohols; alkyl- and/or alkenyl ether phosphates of the formula $RO(C_2H_4O)_xP(=O)(OH)(OR')$, where R is an aliphatic, optionally hydrocarbon residue comprising 8 to 30 carbon atoms, R' is hydrogen, a residue $(CH_2CH_2O)_yR$ and x and y are independent of one other and stand for a number from 1 to 10; sulfated fatty acid alkylene glycol esters of the formula $RC(O)O(alkO)_nSO_3H$, in which R is a linear or branched, aliphatic, saturated and/or unsaturated alkyl residue comprising from 6 to 22 carbon atoms, alk is $CH_2CH_2$, $CHCH_3CH_2$ and/or $CH_2CHCH_3$ and n is a number from about 0.5 to about 5; as well as monoglyceride sulfates and monoglyceride ether sulfates. Particularly preferable cosmetic compositions in terms of the present disclosure are characterized in that they additionally contain at least one anionic surfactant. Preferable anionic surfactants are fatty acids, alkyl sulfates, alkyl ether sulfates and ether carboxylic acids comprising 10 to 20 carbon atoms in the alkyl group and up to 16 glycol ether groups in the molecule. Particularly preferable are $C_8C_{20}$-alkyl sulfates, in particular sodium cetearyl sulfate and sodium lauryl sulfates as well as $C_8C_{20}$-alkyl ether sulfates comprising from 2 to 12, preferably from 2 to 4 ethylene oxide groups, in particular sodium lauryl ether sulfate (INCI: Sodium Laureth Sulfate). The proportion by weight of the anionic surfactant preferably consists of from about 0.1 to about 8.0% by weight, preferably from about 0.1 to about 4.0% by weight, and in particular from about 0.1 to about 2.0% by weight based on the total weight of the formulation (B).

Furthermore, preferred emulsifiers are PEG derivatives of hydrogenated castor oil, for example available under the name PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil. The use of PEG-40 Hydrogenated Castor Oil is preferable in terms of the present disclosure. It is preferably contained in a quantity from about 0.05 to about 1.5% by weight, preferably from about 0.1 to about 1.0% by weight, likewise preferably from about 0.2 to about 0.8% by weight or from about 0.3 to about 0.6% by weight.

To a surprising extent, the preferable emulsifiers and surface-active agents described earlier improve both the cosmetic performance of the inventive compositions as well as their dissolution and application behavior.

In order to enable the application mixture made from formulation (A) and (B) to be applied cleanly and to a restricted area, it has proved to be advantageous for the composition to have an increased viscosity. It is advantageous in this regard if the composition is not present as a paste, viscous cream or thickened gel, but rather possesses sufficient flowability. Furthermore, once made ready for use, the composition must possess rheological properties allowing it to be applied to the fibers to be bleached while at the same time keeping the composition from running or flowing away from the place of action during the period of application. Therefore, the application mixtures preferably have a viscosity of from about 5 to about 100 Pa·s, preferably from about 10 to about 50 Pa·s, in particular from about 10 to about 20 Pa·s, and particularly preferably from about 10 to about 16 Pa·s (Brookfield, 22° C., #5 spindle, 4 rpm). For this purpose, preferable formulations (B) contain at least one thickening agent and/or at least one gelling agent. Corresponding methods as contemplated herein in which the composition (B) additionally contains at least one thickening agent and/or at least one gelling agent are preferable in terms of the present disclosure. Inorganic as well as organic substances are suitable as thickening agents or gelling agents.

The thickening agent can, for example, be selected from among the following polymeric thickening agents known by their INCI names: Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, Astragalus Gummifer Gum, Attapulgite, Avena Sativa (Oat) Kernel Flour, Bentonite, Butoxy Chitosan, Caesalpinia Spinosa Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, Cyamopsis Tetragonoloba (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, Glycine Soja (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/ Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, Solanum Tuberosum (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, Triticum Vulgare (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, Zea Mays (Corn) Starch.

Particularly preferable are polymeric thickeners chosen from among polymeric, anionic, amphiphilic thickeners, most preferably those with the INCI names Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylates/Steareth-20 Methacrylate Crosspolymer.

The polymeric thickening agents are preferably contained in the formulation (B) in a quantity about 0.5 to about 20% by weight, in particular from about 0.5 to about 10% by weight.

It has proven to be particularly advantageous to adjust the viscosity of the application mixture obtained from mixing the compositions (A) and (B) by selecting a suitable polymer blend for the water-soluble film. Thus, the viscosity of the application mixture, the application properties thereof, and the bleaching action can be advantageously influenced by both the chemical nature of the polymer blend and by the quantity of the polymer blend used for the packaging. Therefore, preferable cosmetic compositions are characterized in that the proportion by weight of the polymer blend with the multimodal molecular weight distribution is from about 1 to about 15% by weight, preferably from about 2 to about 10% by weight, and in particular is from about 3 to about 8% by weight of the total weight of the formulations (A) and (B), including the water-soluble film.

Furthermore, the formulation (B) may contain additional active ingredients, auxiliaries and additives, such as nonionic polymers, for example vinylpyrrolidone/vinyl acrylate copolymers, polyvinylpyrrolidone and vinylpyrrolidone/vinyl acetate copolymers and polysiloxanes, cationic polymers, for example quaternized cellulose ethers, polysiloxanes having quaternary groups, dimethyldiallylammonium chloride polymers, acrylamide/dimethyl diallyl ammonium chloride copolymers, dimethylaminoethylmethacrylate/vinylpyrrolidone copolymers quaternized with diethyl sulfate, vinylpyrrolidone/imidazolinium methochloride copolymers, and quaternized polyvinyl alcohol, zwitterionic and amphoteric polymers, for example, acrylamidopropyl-tri-methyl ammonium chloride/acrylate copolymers and octylacrylamide/methyl methacrylate/tert-butylaminoethyl methacrylate/2-hydroxypropyl methacrylate copolymers, anionic polymers, for example polyacrylic acids, cross-linked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers, and acrylic acid/ethyl acrylate/N-tert.butyl-acrylamide terpolymers, solvents and solubilizers such as ethanol, isopropanol, ethylene glycol, propylene glycol, glycerin and diethylene glycol, consistency enhancers such as sugar esters, polyolesters or polyol alkyl ethers, stabilizing agents for hydrogen peroxide, for example complexing agents such as EDTA, NTA, $\alpha$-alaninediacetic acids, and phosphonic acids.

Regarding the application properties of the cosmetic composition as contemplated herein, it has proven advantageous to reduce the proportion by weight of hydrophobic components in the formulation (B) as much as possible. Therefore, preferable cosmetic compositions are characterized in that, based on its weight, formulation (B) contains less than about 20% by weight, preferably less than about 10% by weight, and in particular less than about 5.0% by weight fatty substances. In terms of the present disclosure, fatty substances include those compounds less than 1 g of which can dissolve in 100 g of water at 20° C. Include among these are, for example, waxes such as candelilla wax, carnauba wax or beeswax, shea butter, coconut oil, C12 to C20 fatty acids (in particular palmitic acid, stearic acid), silicones and paraffins.

As initially stated, cosmetic compositions as contemplated herein are particularly suitable for the production of hair bleaching compositions. Therefore, a further object of the present disclosure is a method for changing the color of keratinic fibers in which at least two separately packaged compositions (A) and (B) are mixed immediately prior to application to give an application mixture, and in which the formulation (A) packaged in a water-soluble film is dissolved and incorporated into the formulation (B), whereby the composition (A), based on its total weight, contains from about 10 to about 99% by weight peroxydisulfate(s)

the formulation (B) is a flowable composition comprising water and at least one oxidizing agent, characterized in that formulation (A) has been packaged in a water-soluble film consisting, based on its total weight, to an extent of at least about 60% by weight of a polymer mixture having a multimodal molecular weight distribution.

The inventive compositions, uses and methods, and some preferred embodiments thereof are characterized by the following points:

1. Cosmetic composition for lightening the color of keratinic fibers, containing at least two separately packaged formulations (A) and (B), which are mixed immediately prior to application to give an application mixture, whereby
   the composition (A), based on its total weight, contains from about 10 to about 99% by weight peroxydisulfate(s)
   the formulation (B) is a flowable composition comprising water and at least one oxidizing agent,
   characterized in that formulation (A) has been packaged in a water-soluble film consisting, based on its total weight, to an extent of at least about 60% by weight of a polymer mixture having a multimodal molecular weight distribution.
2. Cosmetic compositions according to point 1, characterized in that the water-soluble film consists, based on its total weight, to an extent of at least about 70% by weight, preferably to an extent of at least about 80% by weight, more preferably to an extent of at least about 90% by weight, and in particular to an extent of at least about 95% by weight of a polymer mixture having a multimodal molecular weight distribution.
3. Cosmetic compositions according to any of the preceding points, characterized in that the polymer blend consists, based on its total weight, of a mixture comprising at least about 60% by weight, preferably at least about 80% by weight, more preferably at least about 90% by weight, quite preferably at least about 95% by weight
   a1) water-soluble vinyl alcohol/vinyl acetate copolymer a1) and
   a2) at least one water-soluble vinyl alcohol/vinyl acetate copolymer a2) different from the water-soluble vinyl alcohol/vinyl acetate copolymer a1).
4. Cosmetic compositions according to any of the preceding points, characterized in that the polymer blend consists, based on its total weight, of a mixture comprising at least about 60% by weight, preferably at least about 80% by weight, more preferably at least about 90% by weight, quite preferably at least about 95% by weight
   a1) water-soluble vinyl alcohol/vinyl acetate copolymer a1) and
   a2) at least one optionally modified water-soluble polysaccharide, preferably at least one water-soluble polysaccharide from the group consisting of methyl cellulose, carboxymethyl cellulose, ethyl cellulose, hydroxyethyl cellulose, hydroxypropyl cellulose, hydroxypropyl methylcellulose, dextrin, and hydroxypropyl starch, quite preferably at least one water-soluble polysaccharide from the group consisting of hydroxypropyl starches.
5. Cosmetic compositions according to any of the previous points, characterized in that the polymer mixture has a polydispersity index of greater than about 2.2, preferably greater than about 3.0, and in particular greater than about 4.6.
6. Cosmetic compositions according to any of the previous points, characterized in that the vinyl alcohol/vinyl acetate copolymer a1) has a polydispersity index of between about 1.8 and about 2.3.
7. Cosmetic compositions according to any of the previous points, characterized in that the vinyl alcohol/vinyl acetate copolymer a1) has a degree of hydrolysis between about 84% and about 90%, preferably between about 85% and about 89%, and in particular between about 86% and about 88%.
8. Cosmetic compositions according to any of the previous points, characterized in that the vinyl alcohol/vinyl acetate copolymer a1) has a viscosity (20° C., 4% by weight solution in water, measured using a Brookfield LV Viscosimeter with UL adapter) of between about 12 cP and about 20 cP, preferably between about 14 cP and about 19 cP, and in particular between about 16 cP and about 18 cP.
9. Cosmetic compositions according to any of the previous points, characterized in that the vinyl alcohol/vinyl acetate copolymer a2) has a viscosity (20° C., 4% by weight solution in water, measured using a Brookfield LV Viscosimeter with UL adapter) of between about 20 cP and about 30 cP, preferably between about 20 cP and about 28 cP, and in particular between about 20 cP and about 25 cP.
10. 10. Cosmetic compositions according to any of the previous points, characterized in that the water-soluble film, based on its total weight, has a water content of from about 3.0 to about 12% by weight, preferably from about 4.0 to about 10% by weight.
11. Cosmetic compositions according to any of the previous points, characterized in that the water-soluble film has a thickness of from about 0.01 to about 0.1 mm, preferably from about 0.01 to about 0.08 mm, and in particular from about 0.02 to about 0.06 mm.
12. Cosmetic compositions according to any of the preceding points, characterized in that the weight ratio of formulation (A) to formulation (B) is from about 2:1 to about 1:100, preferably from about 2:1 to about 1:10, and in particular from about 2:1 to about 1:3.
13. Cosmetic compositions according to any of the preceding points, characterized in that formulation (A), based on its weight, contains from about 15 to about 99% by weight, more preferably from about 20 to about 45% by weight peroxydisulfate(s).
14. Cosmetic compositions according to any of the preceding points, characterized in that formulation (A), based on its weight, contains from about 10 to about 80% by weight, preferably from about 25 to about 70% by weight, more preferably from about 40 to about 60% by weight potassium peroxydisulfate.
15. Cosmetic compositions according to any of the preceding points, characterized in that the ratio by weight of the quantity of potassium peroxydisulfate contained in the composition to the total quantity of peroxydisulfates contained in the composition is at least about 0.5, preferably at least about 0.7, and more preferably at least about 0.9.
16. Cosmetic composition according to one of the preceding points, characterized in that preparation (B), based on its weight, comprises from about 50 to about 98% by weight, preferably from about 60 to about 95% by weight, more preferably from about 80 to about 95% by weight water, and, calculated as 100% H2O2, from about 0.5 to about 20% by weight, preferably from about 1 to about 15% by weight, and particularly preferably from about 2 to about 12% by weight hydrogen peroxide.
17. Cosmetic compositions according to any of the preceding points, characterized in that formulation (B), based on its weight, contains less than about 20% by weight, preferably less than about 10% by weight, and in particular less than about 5.0% by weight fatty substances.

18. Method for changing the color of keratinic fibers, in which at least two separately packaged formulations (A) and (B) are mixed immediately prior to application to give an application mixture, and in which the formulation (A), packaged in a water-soluble film, is dissolved and incorporated into the formulation (B), whereby the composition (A), based on its total weight, contains from about 10 to about 99% by weight peroxydisulfate(s)

the formulation (B) is a flowable composition comprising water and at least one oxidizing agent, characterized in that formulation (A) has been packaged in a water-soluble film consisting, based on its total weight, to an extent of at least about 60% by weight of a polymer mixture having a multimodal molecular weight distribution.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for lightening the color of keratinic fibers, comprising at least two separately packaged formulations (A) and (B), which are mixed immediately prior to application to give an application mixture, whereby the formulation (A), based on its total weight, comprises from about 20 to about 45% by weight peroxydisulfate(s) and is solid, the formulation (B) is a flowable composition comprising about 80 to about 95 percent by weight of water and 2 to 12 percent by weight of hydrogen peroxide calculated as 100% $H_2O_2$, wherein formulation (A) has been packaged in a water-soluble film having a water content of from about 4 to about 10% by weight and comprising, based on its total weight, at least about 95% by weight of a polymer mixture having a multimodal molecular weight distribution wherein the polymer mixture comprises, based on its total weight, at least about 95% by weight of:

a1) water-soluble vinyl alcohol/vinyl acetate copolymer a1) and a2) at least one optionally modified water-soluble polysaccharide chosen from the group of methyl cellulose, carboxymethyl cellulose, ethyl cellulose, hydroxyethyl cellulose, hydroxypropyl cellulose, hydroxypropyl methylcellulose, dextrin, and hydroxypropyl starch, wherein the polymer mixture has a polydispersity index of greater than 4.6, wherein the water-soluble vinyl alcohol/vinyl acetate copolymer a1) has a polydispersity index between about 1.8 and about 2.3, a degree of hydrolysis between about 86% and about 88%, and a Brookfield viscosity between about 14 cP and about 19 cP as measured using a Brookfield LV viscometer with a UL adapter at 20° C., in a 4% by weight solution in water, wherein a weight ratio of the formulation (A) and the formulation (B) is from about 2:1 to about 1:3, wherein the polymer mixture is present in an amount of from about 3 to about 8% by weight of a total weight of the formulation (A) and the formulation (B), including the water-soluble film, and wherein the polymer mixture has a viscosity of from about 10 to about 16 Pa·s as measured using a Brookfield viscometer at 22° C. using a #5 spindle at 4 RPM.

2. The cosmetic composition according to claim 1, wherein the water-soluble film has a thickness from about 0.01 to about 0.1 mm.

3. The cosmetic composition according to claim 1, wherein, based on its weight, formulation (B) comprises less than about 20% by weight fatty substances.

4. A method for changing the color of keratinic fibers, wherein the method comprises mixing at least two separately packaged formulations (A) and (B) immediately prior to application to give an application mixture, in which the formulation (A), packaged in a water-soluble film, is dissolved and incorporated into the formulation (B), whereby the formulation (A), based on its total weight, comprises from about 20 to about 45% by weight peroxydisulfate(s) and is solid, the formulation (B) is a flowable composition comprising about 80 to about 95 percent by weight of water and 2 to 12 percent by weight of hydrogen peroxide calculated as 100% $H_2O_2$, wherein formulation (A) has been packaged in a water-soluble film having a water content of from about 4 to about 10% by weight and comprising, based on its total weight, at least about 95% by weight of a polymer mixture having a multimodal molecular weight distribution wherein the polymer mixture comprises, based on its total weight, at least about 95% by weight of:

a3) water-soluble vinyl alcohol/vinyl acetate copolymer a1) and a4) at least one optionally modified water-soluble polysaccharide chosen from the group of methyl cellulose, carboxymethyl cellulose, ethyl cellulose, hydroxyethyl cellulose, hydroxypropyl cellulose, hydroxypropyl methylcellulose, dextrin, and hydroxypropyl starch, wherein the polymer mixture has a polydispersity index of greater than 4.6, wherein the water-soluble vinyl alcohol/vinyl acetate copolymer a1) has a polydispersity index between about 1.8 and about 2.3, a degree of hydrolysis between about 86% and about 88%, and a viscosity between about 16 cP and about 18 cP as measured using a Brookfield LV viscometer with a UL adapter at 20° C., in a 4% by weight solution in water, and wherein a weight ratio of the formulation (A) and the formulation (B) is from about 2:1 to about 1:3, wherein the polymer mixture is present in an amount of from about 3 to about 8% by weight of a total weight of the formulation (A) and the formulation (B), including the water-soluble film, and wherein the polymer mixture has a viscosity of from about 10 to about 16 Pa·s as measured using a Brookfield viscometer at 22° C. using a #5 spindle at 4 RPM.

5. The cosmetic composition according to claim 1, wherein the water-soluble film has a thickness from about 0.02 to about 0.06 mm.

6. The cosmetic composition according to claim 1, wherein, based on its weight, formulation (B) comprises less than about 5.0% by weight fatty substances.

7. The cosmetic composition according to claim 1, wherein the composition (B) comprises at least one thickening agent and/or at least one gelling agent in an amount of from about 0.5 to about 10% by weight of the formulation (B).

8. The cosmetic composition according to claim 1, wherein the formulation (A) comprises one or more water-soluble polymers chosen from polyvinylpyrrolidone, polyethylene oxide, gelatin, and acetalized compounds thereof.

9. A cosmetic composition for lightening the color of keratinic fibers, comprising at least two separately packaged formulations (A) and (B), which are mixed immediately prior to application to give an application mixture, whereby
the formulation (A), based on its total weight, comprises from about 20 to about 45% by weight peroxydisulfate(s) and is solid,
the formulation (B) is a flowable composition comprising about 80 to about 95 percent by weight of water, 2 to 12 percent by weight of hydrogen peroxide calculated as 100% $H_2O_2$, and at least one thickening agent and/or at least one gelling agent in an amount of from about 0.5 to about 10% by weight of the formulation (B),
wherein formulation (A) has been packaged in a water-soluble film having a water content of from about 4 to about 10% by weight and comprising, based on its total weight, at least about 95% by weight of a polymer mixture having a bimodal molecular weight distribution wherein the polymer mixture comprises, based on its total weight, at least about 95% by weight of:
a1) water-soluble vinyl alcohol/vinyl acetate copolymer a1) and
a2) at least one optionally modified water-soluble polysaccharide chosen from the group of methyl cellulose, carboxymethyl cellulose, ethyl cellulose, hydroxyethyl cellulose, hydroxypropyl cellulose, hydroxypropyl methylcellulose, dextrin, and hydroxypropyl starch,
wherein the polymer mixture has a polydispersity index of greater than 4.6,
wherein the water-soluble vinyl alcohol/vinyl acetate copolymer a1) has a polydispersity index between about 1.8 and about 2.3, a degree of hydrolysis between about 86% and about 88%, and a Brookfield viscosity between about 16 cP and about 18 cP as measured using a Brookfield LV viscometer with a UL adapter at 20° C., in a 4% by weight solution in water, and
wherein a weight ratio of the formulation (A) and the formulation (B) is from about 2:1 to about 1:3,
wherein the polymer mixture is present in an amount of from about 3 to about 8% by weight of a total weight of the formulation (A) and the formulation (B), including the water-soluble film,
wherein the polymer mixture has a viscosity of from about 10 to about 16 Pa·s as measured using a Brookfield viscometer at 22° C. using a #5 spindle at 4 RPM, and
wherein the bimodal molecular weight distribution comprises at least two maxima wherein molecular weights of the at least two maxima differ from about 20% to about 60% based on the smallest identifiable modal molecular weight and a frequency of the minimum found between the at least two maxima differ from the frequency of the smaller of the at least two maxima from about 20% to about 40%, each based on the frequency of the smaller of the two maxima.

10. The cosmetic composition according to claim 9, wherein, based on its weight, formulation (B) comprises less than about 20% by weight fatty substances.

11. The cosmetic composition according to claim 9, wherein, based on its weight, formulation (B) comprises less than about 10% by weight fatty substances.

12. The cosmetic composition according to claim 9, wherein, based on its weight, formulation (B) comprises less than about 5% by weight fatty substances.

13. The cosmetic composition according to claim 1, wherein the formulation (A) comprises one or more water-soluble polymers chosen from polyvinylpyrrolidone, polyethylene oxide, gelatin, and acetalized compounds thereof.

* * * * *